(12) United States Patent
Butterfield et al.

(10) Patent No.: US 12,727,868 B2
(45) Date of Patent: Sep. 8, 2026

(54) RETRACTORS

(71) Applicant: SURE RETRACTORS LIMITED, Glasgow (GB)

(72) Inventors: Forbes Butterfield, Glasgow (GB); David Crosland, Edinburgh (GB)

(73) Assignee: SURE RETRACTORS LIMITED, Glasgow (GB)

( * ) Notice: Subject to any disclaimer, the term of this patent is extended or adjusted under 35 U.S.C. 154(b) by 50 days.

(21) Appl. No.: 18/580,140

(22) PCT Filed: Aug. 10, 2022

(86) PCT No.: PCT/GB2022/052087
§ 371 (c)(1),
(2) Date: Jan. 17, 2024

(87) PCT Pub. No.: WO2023/017266
PCT Pub. Date: Feb. 16, 2023

(65) Prior Publication Data

US 2025/0032109 A1 Jan. 30, 2025

(30) Foreign Application Priority Data

Oct. 8, 2021 (GB) ..................................... 2111487
Jan. 28, 2022 (GB) ..................................... 2201162

(51) Int. Cl.
*A61B 17/02* (2006.01)
*A61B 17/00* (2006.01)

(52) U.S. Cl.
CPC ...... *A61B 17/0206* (2013.01); *A61B 17/0293* (2013.01); *A61B 2017/00858* (2013.01)

(58) Field of Classification Search
CPC ................ A61B 17/02; A61B 17/0206; A61B 2017/00858
See application file for complete search history.

(56) References Cited

U.S. PATENT DOCUMENTS 4,926,849 A 5/1990 Downey
5,704,937 A 1/1998 Martin
(Continued)

FOREIGN PATENT DOCUMENTS

CN 109788947 A * 5/2019 ........... A61B 17/083
EP 0951868 10/1999
(Continued)

OTHER PUBLICATIONS

Search Report for GB Application No. GB1718242.9.
(Continued)

*Primary Examiner* — Jacqueline T Johanas
(74) *Attorney, Agent, or Firm* — LIU & LIU

(57) ABSTRACT

The invention relates to a surgical retractor (10) comprising a support (12), first and second arms (14, 16) extending from a same side of the support, a first anatomy engaging member (42) having a first interior face (52) and a first exterior face (50), and a second anatomy engaging member (44) having a second interior face (52) and a second exterior face (50). The first anatomy engaging member (42) depends along its length from the first arm (14) whereby the first exterior face faces (50) away from the second anatomy engaging member (44). The second anatomy engaging member (44) depends along its length from the second arm (16) whereby the second exterior face (50) faces away from the first anatomy engaging member (42). Each of the first and second exterior faces (50) defines at least one elongate protrusion, the elongate protrusion extending transversely on the respective anatomy engaging member. The first and second arms (14, 16) are spaced apart from each other along the support (12).

22 Claims, 4 Drawing Sheets

(56) References Cited

U.S. PATENT DOCUMENTS 5,779,629 A 7/1998 Hohlen
6,102,854 A 8/2000 Cartier et al.
6,464,634 B1 * 10/2002 Fraser ................ A61B 17/0293 600/233
6,468,207 B1 * 10/2002 Fowler, Jr. ......... A61B 17/0293 600/233
9,028,522 B1 5/2015 Prado
9,084,591 B2 7/2015 Reglos et al.
9,386,971 B1 7/2016 Casey
9,675,332 B2 * 6/2017 Beck .................. A61B 17/0281
2002/0077532 A1 6/2002 Gannoe et al.
2003/0225416 A1 * 12/2003 Bonvallet ............ A61B 17/025 606/205
2004/0049188 A1 3/2004 Slivka et al.
2010/0222644 A1 * 9/2010 Sebastian ........... A61B 17/0206 600/228
2011/0144450 A1 * 6/2011 Paolitto .............. A61B 17/0206 600/224
2012/0022335 A1 * 1/2012 Assaker ............. A61B 17/0206 600/225
2012/0130180 A1 * 5/2012 Pell .................... A61B 17/0206 600/206
2012/0265302 A1 * 10/2012 Beger ....................... A61F 2/44 623/17.11
2012/0283521 A1 11/2012 Smith et al.
2013/0237766 A1 9/2013 Pell et al.
2014/0142699 A1 * 5/2014 Beger ....................... A61F 2/44 623/17.11
2014/0323811 A1 * 10/2014 DeSantis ................ A61B 17/02 600/245
2014/0364698 A1 * 12/2014 Nadershahi ............ A61B 1/303 600/215
2015/0209022 A1 * 7/2015 Ruppert ............. A61B 17/0206 600/219
2015/0257746 A1 * 9/2015 Seifert ............... A61B 17/3462 600/206
2015/0313642 A1 11/2015 Fessler
2016/0151058 A1 * 6/2016 Ferro ..................... A61B 17/02 600/215
2017/0042524 A1 * 2/2017 Angus ................ A61B 17/0206
2017/0215858 A1 8/2017 Haque et al.
2018/0214189 A1 8/2018 Olea et al.
2018/0271507 A1 9/2018 Gasser
2018/0296203 A1 10/2018 Powley et al.
2019/0059869 A1 2/2019 Avalos et al.
2019/0254771 A1 * 8/2019 Swift ..................... A61B 90/30
2019/0374214 A1 * 12/2019 Bohl ...................... A61B 90/50
2020/0187929 A1 * 6/2020 DeHeer .............. A61B 17/0218
2020/0253594 A1 * 8/2020 Wilson ............... A61B 17/7074
2020/0253595 A1 * 8/2020 McBride, Jr. .......... A61B 34/30
2020/0261116 A1 * 8/2020 Long ...................... A61B 1/303
2020/0337689 A1 * 10/2020 Butterfield ......... A61B 17/0206
2022/0039786 A1 * 2/2022 Dewey ................. A61B 17/025
2022/0142632 A1 * 5/2022 Simon ................ A61B 17/0293
2025/0032109 A1 * 1/2025 Butterfield ......... A61B 17/0293
2025/0032110 A1 * 1/2025 Butterfield .............. A61L 31/10

FOREIGN PATENT DOCUMENTS

EP 2168503 A1 * 3/2010 ......... A61B 17/0206
EP 2394584 A1 * 12/2011 ......... A61B 17/0206
EP 2394584 B1 * 4/2014 ......... A61B 17/0206
GB 1008555 10/1965
GB 2547792 8/2017
GB 2547792 A * 8/2017 ......... A61B 17/0206
GB 2566559 A * 3/2019 ......... A61B 17/0206
WO 2014/018624 1/2014
WO WO-2023017266 A1 * 2/2023 ......... A61B 17/0206
WO WO-2023111545 A1 * 6/2023 ......... A61B 17/0206

OTHER PUBLICATIONS

International Search Report for International Application No. PCT/GB2018/053199.
International Search Report for counterpart International Application No. PCT/GB2022/052087.

* cited by examiner 117
119
217
134
132
144
182
124
228
182
222
228
226
130
116
122
220
110
228
128
35
212
126
224
182
118
120
142
228
178
182
114
182

RETRACTORS

FIELD OF THE INVENTION

The present invention relates to surgical retractors and methods of surgery involving such surgical retractors.

BACKGROUND ART

Surgical retractors are known. Surgical retractors separate the edges of an incision or wound, and perhaps also hold back underlying organs and tissues, to allow better visibility of and access to anatomy under the incision or wound.

The present inventors have become appreciative of shortcomings of known surgical retractors. The present invention has been devised in light of the inventors' appreciation of such shortcomings. It is therefore an object for the present invention to provide an improved surgical retractor comprising a support, first and second arms extending from the support, and first and second anatomy engaging members depending from the first and second arms respectively.

It is a further object for the present invention to provide a method of surgery on a human or animal subject involving use of a surgical retractor which comprises a support, first and second arms extending from the support, and first and second anatomy engaging members depending from the first and second arms respectively.

STATEMENT OF INVENTION

According to a first aspect of the present invention there is provided a surgical retractor comprising:

- a support;
- a first arm extending from the support;
- a second arm extending from the support, the first and second arms extending from a same side of the support;
- a first anatomy engaging member having a first interior face and a first exterior face; and
- a second anatomy engaging member having a second interior face and a second exterior face, wherein
- the first anatomy engaging member depends along its length from the first arm whereby the first exterior face faces away from the second anatomy engaging member;
- the second anatomy engaging member depends along its length from the second arm whereby the second exterior face faces away from the first anatomy engaging member;
- each of the first and second exterior faces defines at least one elongate protrusion, the elongate protrusion extending transversely on the respective anatomy engaging member; and
- the first and second arms are spaced apart from each other along the support.

The surgical retractor comprises a support and first and second arms. The first and second arms extend from a same side of the support. The surgical retractor comprises first and second anatomy engaging members. The first anatomy engaging member has a first interior face and a first exterior face, and the second anatomy engaging member has a second interior face and a second exterior face. The first anatomy engaging member depends along its length from the first arm whereby the first exterior face faces away from the second anatomy engaging member. The first anatomy engaging member may therefore depend from the first arm in a longitudinal direction of the first anatomy engaging member. The second anatomy engaging member depends along its length from the second arm whereby the second exterior face faces away from the first anatomy engaging member. The second anatomy engaging member may therefore depend from the second arm in a longitudinal direction of the second anatomy engaging member. The first and second exterior faces may be generally and more specifically substantially oppositely directed. Each of the first and second exterior faces defines at least one elongate protrusion, the elongate protrusion extending transversely on the respective anatomy engaging member. The elongate protrusion may therefore extend in a direction orthogonal to the longitudinal direction of the first anatomy engaging member. The first and second arms are spaced apart from each other along the support. The first and second interior faces may therefore be spaced apart from each other. Each of the first and second arms may extend from a respective location, the two locations spaced apart from each other along the support. The support may be elongate and the first and second arms may extend from respective locations on the elongate support, the respective locations spaced apart from each other along the longitudinal direction of the elongate support.

The first and second arms may be mechanically coupled to the support whereby separation between the first and second arms is substantially fixed. More specifically, the first and second arms may be attached to the support so that the first and second arms do not move along the support. Such attachment may not exclude movement of at least one of the first and second arms relative to the support but such that separation between the first and second arms is substantially fixed. For example, at least one of the first and second arms may be rotatable around the support.

Alternatively, the surgical retractor may be configured for change in separation between the first and second arms along the support, such as by way of clinician operation, whereby separation between the first and second exterior faces is changed. Change in separation between the first and second arms may be by movement of at least one of the first and second arms along the support whereby there is change in extent of spacing apart of the first and second arms along the support.

In use, separation between the first and second arms of the surgical retractor may be set to allow the first and anatomy engaging members to be received readily in an incision or wound. The clinician may then increase separation between the first and second arms whereby the first exterior face of the first anatomy engaging member bears against a first side of the incision or wound and the second exterior face of the second anatomy engaging member bears against a second, opposite side of the incision or wound. The incision or wound may thus be retracted.

The inventors have found that known surgical retractors which lack at least one elongate protrusion extending transversely on the exterior face of each of two anatomy engaging members tend to be pushed out of the incision or wound by pressure from the tissue being retracted. This problem tends to be more marked when tissue capable of exerting greater force, such as muscle tissue, is being retracted. Nevertheless, the problem may be evident even when more yielding tissue, such a skin, is being retracted and in particular when yielding tissue is retracted for considerable time or where the tissue is tauter.

The at least one elongate protrusion defined by each of the first and second exterior faces may engage, and more specifically may interengage, with the tissue being retracted to present resistance to relative movement of the first and second anatomy engaging members and the tissue being retracted in the longitudinal direction of the first and second anatomy engaging members. The elongate protrusion may engage with the tissue by pressing into the tissue or by fitting underneath tissue whereby the elongate protrusion and the tissue interlock. The at least one elongate protrusion defined by each of the first and second exterior faces may thus present resistance to the first and second anatomy engaging members being pushed out of the incision or wound.

The elongate protrusion may be defined by first and second protrusion sides and a protrusion land, the first and second protrusion sides extending up from the respective exterior face, and the protrusion land extending between the distal end of the first protrusion side and the distal end of the second protrusion side. The first and second protrusion sides may be generally parallel, and more specifically may be substantially parallel with each other.

The protrusion land may be substantially linear in the longitudinal direction of the respective anatomy engaging member. Alternatively or in addition, the protrusion land may be arcuate in the transverse direction. Curvature of the protrusion land may be greatest towards each end of the protrusion land. The protrusion land may be convex. The height of the first and second protrusion sides may therefore decrease as one moves towards the ends of the protrusion. More specifically, the height of the first and second protrusion sides may decrease to substantially zero at each end of the protrusion land. Each end of the protrusion may thus be of a shape which presents less risk of trauma to tissue. Furthermore, the ends of the protrusion may thus be shaped to provide for ease of movement in the transverse direction of the respective anatomy engaging member relative to tissue. Relative transverse movement of the anatomy engaging member and the tissue may be by way of movement of tissue, such as tissue movement during settlement of retracted tissue, by way of movement of the surgical retractor, or by way of movement of the anatomy engaging member relative to the respective arm. Relative movement of anatomy engaging member and the respective arm is described further below.

The protrusion may define an acute angle with the respective exterior face. More specifically the acute angle may be defined between a part of the exterior face on the side of the protrusion nearer to a proximal end of the anatomy engaging member than a part of the exterior face on the other side of the protrusion. The protrusion may therefore protrude away from the exterior face and in a direction away from a distal end of the anatomy engaging member. A protrusion which defines such an acute angle may more readily capture and hold tissue. The acute angle may be no more than 60 degrees, 50 degrees, 40 degrees, 30 degrees or 20 degrees. The acute angle may be at least 10 degrees, 20 degrees, 30 degrees, 40 degrees or 50 degrees. The inventors have found that an acute angle of between 25 degrees and 35 degrees and more specifically of 30 degrees may provide for effective engagement with certain types of tissue.

Alternatively or in addition, the protrusion may define an obtuse angle with the respective exterior face. More specifically the obtuse angle may be defined between a part of the exterior face on the side of the protrusion nearer to a distal end of the anatomy engaging member than a part of the exterior face on the other side of the protrusion. A protrusion which defines such an obtuse angle may move more readily over tissue in the longitudinal direction, and more specifically when tissue is moving towards the respective arm, without interengaging with the tissue. The anatomy engaging member may therefore be inserted into the incision or wound more readily, such as with less likelihood of tissue being snagged by the protrusion. The obtuse angle may be at least 120 degrees, 130 degrees, 140 degrees, 150 degrees or 160 degrees. The obtuse angle may be no more than 170 degrees, 160 degrees, 150 degrees, 140 degrees or 130 degrees. The inventors have found that an obtuse angle of between 145 degrees and 155 degrees and more specifically of 150 degrees may provide for effective movement over certain types of tissue.

At least one of the first and second exterior faces may define plural elongate protrusions, such as four elongate protrusions. The plural elongate protrusions may be spaced apart, and more specifically may be substantially evenly spaced apart, in the longitudinal direction of the respective anatomy engaging member. Plural elongate protrusions may provide for engagement with tissues at different depths in an incision or wound. For example, a first one of the plural elongate protrusions closest to the proximal end of the anatomy engaging member may engage with skin tissue and a second one of the plural elongate protrusions may engage at greater depth with muscle tissue.

The anatomy engaging member may comprise a main body which defines the respective exterior and interior faces. The main body may have the form of an elongate plate. The main body may be generally and more specifically substantially rectangular when viewed from the interior or exterior face.

The main body or a face thereof may be arcuate. The main body or a face thereof may curve in the transverse direction. Furthermore, the main body or a face thereof may not be curved in the longitudinal direction except perhaps towards at least one of the proximal and distal ends of the main body. The exterior face may be convex. Alternatively or in addition, the interior face may be concave.

The main body may comprise a foot portion at a distal end thereof. The foot portion may extend generally or more specifically substantially orthogonally to the part of the main body from which the foot portion extends. The foot portion may extend on the same side of the main body as the at least one elongate protrusion. In use, the foot portion may sit on anatomy. Alternatively, the foot portion may fit underneath anatomy whereby the anatomy is gathered up and held by the foot portion. The foot portion may be useful for engaging with a substantial mass of anatomy, such as muscle tissue, or perhaps even for fitting underneath bone.

The foot portion may define a nonlinear profile in the transverse direction and at a distal end thereof. The nonlinear profile may be shaped to abut against or perhaps engage with anatomy of correspondingly nonlinear profile. For example, the nonlinear profile may abut against bone or engage with anatomy of more unyielding nature, such as muscle tissue. The nonlinear profile may comprise plural recesses, such as two recesses, which are spaced apart across the width of the main body, i.e. in the transverse direction.

As described above, the first and second anatomy engaging members depend from the first and second arms respectively. Furthermore, at least one of the first and second anatomy engaging members may be attached to the respective arm. More specifically the anatomy engaging member may be attached to the respective arm for movement, such as sliding movement, of the anatomy engaging member along the arm.

The anatomy engaging member may be configured such that it extends substantially orthogonally to the respective arm. The anatomy engaging member may be configured to attach releasably to a respective arm. More specifically the anatomy engaging member may define an engaging member profile which provides for mechanical engagement with the respective arm. The engaging member profile and the respective arm may be configured such that the anatomy engaging member is clipped to the arm. The engaging member profile may be defined by an attachment portion of the anatomy engaging member. Where the anatomy engaging member comprises a main body, the main body may be attached at its proximal end to the attachment portion.

The engaging member profile may cooperate with an arm profile, which is defined by the respective arm, to resist separation of the anatomy engaging member from the arm whilst allowing movement of the anatomy engaging member along the arm. The engaging member profile may have a main profile portion which extends across a first surface of the arm, i.e. a surface of the arm furthest from the incision or wound when the retractor is in use. The main profile portion and the first surface of the arm may have corresponding shapes, such as corresponding arcuate shapes, whereby the main profile portion and the first surface are adjacent and more specifically substantially abut against each other. The engaging member profile may have first and second lateral portions at a respective end of the main profile portion, the first and second lateral portions each shaped to extend part way across a second surface of the arm, which is oppositely directed to the first surface. The distal end of the first lateral portion may oppose the distal end of the second lateral portion. The distal ends of the first and second lateral portions may be spaced apart from each other whereby the engaging member profile does not encircle the arm. The anatomy engaging member may be attached to the arm by sliding the engaging member profile over the distal end of the arm. Where the engaging member profile is defined by resilient material, the engaging member profile may be clipped onto the arm by displacing the distal ends of the first and second lateral portion apart from each other to sufficient extent to admit the arm between the displaced distal ends.

The anatomy engaging member may be integrally formed. Alternatively or in addition, the anatomy engaging member may be formed from a plastics material, as described further below.

As described above, the surgical retractor may be configured for change in separation between the first and second arms whereby separation between the first and second exterior faces is changed.

The support may be elongate. The first and second arms may be attached at first and second locations respectively on the elongate support, the first and second locations spaced apart from each other. Furthermore, at least one of the first and second arms may be attached to the elongate support for movement along the elongate support. The separation between the first and second arms may thus be changed to thereby change an extent of retraction achieved by way of engagement of the first and second anatomy engaging members with tissue.

The support and the arm may define cooperating surface profiles which provide for movement of the arm along the support. More specifically, the support may define a screw thread and the arm may define a threaded profile which engages with the screw thread. The support may therefore comprise a screw thread along at least part of its length and the arm may therefore comprise a threaded profile which engages with the screw thread of the support. The support may be of generally cylindrical form. Rotation of the support relative to the arm may drive the arm along the support by way of engagement of threaded profile and screw thread.

Where the first and second arms are movable along the support, the support may define a first screw thread and a second screw thread which extend along different parts of the support. The first screw thread may be in a first half of the support and the second screw thread may be in a second half of the support. The first and second screw threads may run in opposite directions such that each screw thread runs towards its respective end of the support or each screw thread runs way from its respective end of the support.

The first arm may define a first threaded profile and the second arm may define a second threaded profile, the first threaded profile engaging with the first screw thread and the second threaded profile engaging with the second screw thread. Rotation of the support relative to the first and second arms may cause the first and second screw threads to run in opposite directions. When the support is rotated in a first direction the first and second arms may be driven further apart to increase an extent of retraction and when the support is rotated in a second, opposite direction the first and second arms may be driven closer together to reduce an extent of retraction.

At least one of the first and second arms may comprise a proximal portion comprising the respective threaded profile. The proximal portion may be configured to encircle the support. The arm may further comprise an elongate arm member which extends from the proximal portion. The respective anatomy engaging member may depend from the arm member. The arm member may be fixedly attached to the proximal portion. More specifically, the arm member and the proximal portion may be integrally formed.

As described above, change in separation between the first and second arms may be achieved by rotation of the support. In use, the support may be rotated by the clinician. The clinician may use a tool to rotate the support. The support may therefore be shaped to interengage with a tool. More specifically, the support may define, such as at an end of the support, one of a plug and a socket which interengages with the other of a plug and a socket defined by the tool. The tool may comprise a handle which is gripped by the clinician when rotating the support by way of the tool. The handle may be comprised in an end of the tool opposite an end of the tool at which the plug and a socket is defined. The surgical retractor may comprise the tool.

As described above, the at least one elongate protrusion defined by each of the first and second exterior faces may present resistance to the first and second anatomy engaging members being pushed out of the incision or wound. Furthermore, an anatomy engaging member may be formed from a plastics material. The inventors have found that the coefficient of friction of some plastics materials is too high to allow tissue to move sufficiently readily over the surface of the anatomy engaging member. Some degree of ease of movement of tissue over the surface of the anatomy engaging member may be desirable during use of the retractor, such as when the retractor is being inserted into an incision or wound. Also, some degree of ease of movement in the transverse direction of tissue over the surface of the anatomy engaging member may be desirable when the retractor is being sited in the incision or wound and/or when separation between the first and second arms is being changed during retraction.

The inventors have discovered that polyester materials have an appropriate coefficient of friction. The anatomy engaging member may therefore be formed from a polyester material. The at least one elongate protrusion and formation from a polyester material may work together to provide for ease of movement of tissue relative to the anatomy engaging member while reducing risk of the retractor being pushed out of the incision or wound.

More specifically, the anatomy engaging member may be formed from a polycarbonate. The inventors have found polycarbonate to provide a coefficient of friction which is advantageous in certain applications.

Aside from coefficient of friction, stiffness of the plastics material has been discovered to be of significance under certain circumstances. Surgical procedures involving retraction may be of considerable duration. Retracted tissue may therefore be subject to distress over a long period. Tissue damage and perhaps even necrosis may therefore be a risk. The inventors have found some degree of flexure of the anatomy engaging member to be desirable in reducing likelihood of tissue distress. A polyester material, and more specifically a polycarbonate material, has been found to have appropriate flexibility.

Distress caused by the anatomy engaging member pressing unduly against tissue may be indicated by blanching of the tissue. However, known anatomy engaging members obscure tissue blanching from clinician observation. The anatomy engaging member may therefore be formed at least in part from material, and more specifically plastics material, that is transparent in the sense of permitting transmission of light therethrough. The clinician may therefore be able to observe blanching of tissue underneath the anatomy engaging member. Aside from providing for ease of observation of tissue blanching, transparent material may provide for ease of determination of cleanliness of the anatomy engaging member, such as by observation by a clinician.

The transparent material from which the anatomy engaging member is formed may be translucent.

As described above, the anatomy engaging member may comprise a main body. The main body may be formed from transparent material. More specifically, the anatomy engaging member may be formed substantially completely from transparent material. Substantially complete formation of the anatomy engaging member from transparent material may be appropriate where the anatomy engaging member is integrally formed.

The anatomy engaging member may be formed from a material selected from the group consisting of: polyester, and more specifically polycarbonate (PC) or polyethylene terephthalate (PET); acrylonitrile butadiene styrene (ABS); and poly methyl methacrylate (PMMA). In certain circumstances, such as when coefficient of friction and/or stiffness of the anatomy engaging member is a consideration, the anatomy engaging member may be formed from a transparent polycarbonate (PC) material.

At least one part of the surgical retractor other than at least one of the anatomy engaging members may be formed from a plastics material.

The surgical retractor with exception of at least one of the anatomy engaging members may be formed from a plastics material comprising a polyarylamide, such as GS Ixef® 1022 from Solvay S. A. A further exception in this regard may be when an arm, such as one, other or both of the first and second arms, comprises a collar, as described further below, the collar formed from polyoxymethylene (POM). Components of the surgical retractor, such as at least one of the first and second arms and the support, may be formed substantially wholly of a polyarylamide. Where the surgical retractor comprises a tool for rotating the support, the tool may be formed, and perhaps may be substantially wholly formed, of a plastics material. Furthermore, the tool may be formed of a polyester material, and more specifically, a polycarbonate (PC). Use of polycarbonate (PC) for the tool has been found to offer superior characteristics under certain circumstances.

As discussed above, some degree of flexure in anatomy engaging members of retractors may be desirable to reduce likelihood of tissue distress. The surgical retractor described hereinabove may be used in a variety of applications involving different forms and hence robustness of tissue. In one application, the surgical retractor may be a spinal retractor which is typically used for retraction of tissue of a more robust nature. In another application, the surgical retractor may be a cervical retractor. Cervical retractors are used for soft tissue retraction in the like of anterior cervical discectomy and fusion procedures. Flexure of anatomy engaging members may be particularly advantageous for cervical retractors in view of their being involved in retraction of soft tissue.

At least one anatomy engaging member of a cervical retractor may be formed from a material selected from the above described group of materials, i.e. polyester, and more specifically polycarbonate (PC) or polyethylene terephthalate (PET); acrylonitrile butadiene styrene (ABS); and poly methyl methacrylate (PMMA). A polycarbonate material (PC) has been found to have appropriate flexibility for many applications of cervical retractors.

In view of an anatomy engaging member of a cervical retractor pressing against soft tissue, there may be risk of distress being caused to the soft tissue by application of undue pressure. As described above, distress caused by undue pressure exerted by an anatomy engaging member may be indicated by blanching of tissue underneath the anatomy engaging member. At least one anatomy engaging member of a cervical retractor may therefore be formed from a transparent material selected from the aforementioned group of materials. Transparent polycarbonate material (PC) has been found to be particularly advantageous in many applications of cervical retractors.

In view of the smaller operative site in typical applications of a cervical retractor, the cervical retractor may be of smaller size than the earlier described surgical retractor. A maximum spacing between the first and second arms of the cervical retractor may be 50 mm. In contrast, a maximum spacing between the first and second arms of the previously described surgical retractor may be 200 mm. Alternatively or in addition, each of the first and second arms of the cervical retractor may have a maximum length of 80 mm. In contrast, each of the first and second arms of the previously described surgical retractor may have a maximum length of 150 mm. Alternatively or in addition, an anatomy engaging member of the cervical retractor and more specifically a main body of the anatomy engaging member may have a maximum length of 55 mm. In contrast, a main body of an anatomy engaging member of the previously described surgical retractor may have a maximum length of 120 mm.

The threaded profile of the proximal portion of at least one of the first and second arms of the cervical retractor may be integrally formed with the proximal portion. There is therefore no need for a collar to define the threaded profile.

According to a second aspect of the present invention there is provided a method of surgery on a human or animal subject involving use of a surgical retractor which comprises a support, first and second arms extending from a same side of the support, and first and second anatomy engaging members depending along their length from the first and second arms respectively, the first anatomy engaging member having a first interior face and a first exterior face, the second anatomy engaging member having a second interior face and a second exterior face, the first and second anatomy engaging members depending from the first and second arms respectively whereby the first exterior face faces away from the second anatomy engaging member and the second exterior face faces away from the first anatomy engaging member, and the first and second arms are spaced apart from each other along the support, the method of surgery comprising:

disposing the surgical retractor relative to an incision or wound in the human or animal subject and such that the first and second anatomy engaging members are received in the incision or wound, each of the first and second exterior faces defining at least one elongate protrusion which is received in the incision or wound, the elongate protrusion extending transversely on the respective anatomy engaging member, wherein the first exterior face bears against first tissue at one side of the incision or wound and the second exterior face bears against second tissue at another side of the incision or wound, at least one of the first and second tissue is drawn back, and the at least one elongate protrusion on the first and second exterior faces engages with the first and second tissue respectively.

The method of surgery on the human or animal subject is practiced by a clinician, such as a surgeon. The clinician disposes the surgical retractor relative to an incision or wound in the human or animal subject and such that the first and second anatomy engaging members are received in the incision or wound. Each of the first and second exterior faces defines at least one elongate protrusion which is received in the incision or wound. The elongate protrusion extends transversely on the respective anatomy engaging member.

The at least one elongate protrusion on the first and second exterior faces engages with the first and second tissue respectively. The at least one elongate protrusion on the first and second exterior faces may thus present resistance to movement in the longitudinal direction of the first and second anatomy engaging members of the first and second anatomy engaging members relative to the first and second tissue respectively. Positioning of the surgical retractor for engagement of the at least one elongate protrusion on the first and second exterior faces with the first and second tissue may be achieved during one, other or both of the step of disposing the surgical retractor relative to the incision or wound and the step described below of operating the surgical retractor to increase separation between the first and second arms.

The method comprises at least one of the first and second tissue being drawn back, i.e. retracted, by the increase in separation. Whether one, other or both of the first and second tissue is retracted may depend on the nature of the anatomy involved. For example, both of the first and second tissue may be retracted where the first and second tissue is relatively yielding. By way of another example, one only of the first and second tissue may be retracted where one of the first and second tissue is more yielding, such a skin tissue, and the other of the first and second tissue is unyielding, such as muscle tissue.

The surgical retractor may be configured for change in separation between the first and second arms whereby separation between the first and second exterior faces is changed. The method may therefore further comprise operating the surgical retractor to increase separation between the first and second arms to thereby increase separation between the first and second exterior faces to an extent sufficient for the first exterior face to bear against first tissue at one side of the incision or wound and for the second exterior face to bear against second tissue at another side of the incision or wound. The step of operating the surgical retractor to increase separation between the first and second arms may be carried out after the surgical retractor has been disposed appropriately relative to the incision or wound.

When the need for retraction has passed, the method may further comprise removal of the surgical retractor from the incision or wound, such as by the clinician.

Where the surgical retractor is configured for change in separation between the first and second arms, the method may comprise operating the surgical retractor, such as by a clinician, to decrease separation between the first and second arms to thereby decrease separation between the first and second exterior faces of the anatomy engaging members. The surgical retractor may then be removed from the incision or wound.

Further embodiments of the second aspect of the present invention may comprise one or more features of the first aspect of the present invention.

The inventors have appreciated the use of polyester material for the anatomy engaging member to be of wider applicability than hitherto described. Therefore, and according to a third aspect of the present invention, there is provided a surgical retractor comprising:

a support;

a first arm extending from the support;

a second arm extending from the support, the first and second arms extending from a same side of the support;

a first anatomy engaging member depending from the first arm; and a second anatomy engaging member depending from the second arm, wherein at least one of the first and second anatomy engaging members is formed from a polyester material; and the first and second arms are spaced apart from each other along the support.

The surgical retractor comprises a support from which first and second arms extend. The surgical retractor further comprises first and second anatomy engaging members which depend respectively from the first and second arms. At least one of the first and second anatomy engaging members is formed from a polyester material. Furthermore, the first and second arms are spaced apart from each other along the support.

In use, the surgical retractor is disposed relative to the incision or wound such that the first anatomy engaging member bears against a first side of the incision or wound and the second anatomy engaging member bears against a second, opposite side of the incision or wound. The incision or wound may thus be retracted.

Forming at least one of the first and second anatomy engaging members from a polyester material has been found to confer benefit. The inventors have found that the coefficient of friction of some plastics materials is too high to allow tissue to move sufficiently readily over the surface of the anatomy engaging member. Some degree of ease of movement of tissue over the surface of the anatomy engaging member may be desirable during use of the retractor. The inventors have discovered that polyesters have an appropriate coefficient of friction. In certain circumstances, polycarbonate has been found to be particularly effective. The anatomy engaging member may therefore be formed from a polycarbonate.

Irrespective of the effect of coefficient of friction, stiffness of plastics material has been discovered to be of significance under certain circumstances. Surgical procedures involving retraction may be of considerable duration. Retracted tissue may therefore be subject to distress over a long period.

Tissue damage and perhaps even necrosis may therefore be a risk. The inventors have found some degree of flexure of the anatomy engaging member to be desirable in reducing likelihood of tissue distress. A polyester material, and more specifically a polycarbonate material, has been found to have appropriate flexibility.

The surgical retractor may be configured for change in separation between the first and second arms whereby separation between the first and second anatomy engaging members is changed. In use, the separation between the first and second arms of the surgical retractor may be set to allow the first and anatomy engaging members to be received readily in an incision or wound. The clinician may then increase the separation between the first and second arms whereby the first anatomy engaging member bears against a first side of the incision or wound and the second anatomy engaging member bears against a second, opposite side of the incision or wound. The incision or wound may thus be retracted.

Further embodiments of the third aspect of the present invention may comprise one or more features of the first aspect of the present invention.

According to a fourth aspect of the present invention there is provided a method of surgery on a human or animal subject involving use of a surgical retractor which comprises a support, first and second arms extending from a same side of the support, and first and second anatomy engaging members depending from the first and second arms respectively, the first and second arms spaced apart from each other along the support, the method of surgery comprising:

- disposing the surgical retractor relative to an incision or wound in the human or animal subject and such that the first and second anatomy engaging members are received in the incision or wound, wherein
- the first anatomy engaging member bears against first tissue at one side of the incision or wound and the second anatomy engaging member bears against second tissue at another side of the incision or wound,
- at least one of the first and second tissue is drawn back, and
- at least one of the first and second anatomy engaging members is formed from a polyester material.

The method of surgery on the human or animal subject is practiced by a clinician. The clinician disposes the surgical retractor relative to an incision or wound in the human or animal subject and such that the first and second anatomy engaging members are received in the incision or wound. The method comprises the first anatomy engaging member bearing against first tissue at one side of the incision or wound and the second anatomy engaging member bears against second tissue at another side of the incision or wound. Furthermore, the method comprises at least one of the first and second tissue being drawn back. At least one of the first and second anatomy engaging members is formed from a polyester material.

The method may further comprise the clinician operating the surgical retractor to increase separation between the first and second arms. Increase in separation between the first and second arms may cause increase in separation between the first and second anatomy engaging members comprised in the surgical retractor. The step of operating the surgical retractor to increase separation may be after the surgical retractor has been disposed appropriately relative to the incision or wound.

The clinician may operate the surgical retractor to increase separation between the first and second arms to an extent sufficient for the first anatomy engaging member to bear against first tissue at one side of the incision or wound and for the second anatomy engaging member to bear against second tissue at another side of the incision or wound. The step of operating the surgical retractor to increase separation between the first and second arms further may comprise at least one of the first and second tissue being drawn back, i.e. retracted, by the increase in separation. Whether one, other or both of the first and second tissue is retracted may depend on the nature of the anatomy involved. Formation of at least one of the first and second anatomy engaging members from a polyester material may confer at least one of the benefits described above, i.e. appropriate coefficient of friction, and appropriate extent of flexibility.

Further embodiments of the fourth aspect of the present invention may comprise one or more features of any previous aspect of the present invention.

The inventors have appreciated the use of a transparent material for the anatomy engaging member to be of wider applicability than hitherto described. Therefore, and according to a fifth aspect of the present invention, there is provided a surgical retractor comprising:

- a support;
- a first arm extending from the support;
- a second arm extending from the support, the first and second arms extending from a same side of the support and spaced apart from each other along the support;
- a first anatomy engaging member depending from the first arm; and
- a second anatomy engaging member depending from the second arm, wherein
- at least one of the first and second anatomy engaging members is formed at least in part from a transparent material.

The surgical retractor comprises a support from which first and second arms extend. The first and second arms are spaced apart from each other along the support. The surgical retractor further comprises first and second anatomy engaging members which depend respectively from the first and second arms. At least one of the first and second anatomy engaging members is formed at least in part from a transparent material.

Forming at least one of the first and second anatomy engaging members at least in part from a transparent material has been found to confer benefit. Distress caused by the anatomy engaging member pressing unduly against tissue may be indicated by blanching of the tissue and in particular blanching underneath the anatomy engaging member. However, known anatomy engaging members obscure tissue blanching from clinician observation. Forming at least a part of the anatomy engaging member from material, and more specifically plastics material, that is transparent in the sense of permitting transmission of light therethrough may enable observation of tissue blanching underneath the anatomy engaging member. The clinician may thus be able to determine if too much pressure is being applied to tissue during retraction and take appropriate action. For example, the clinician may replace the current surgical retractor with a surgical retractor of having closer spaced first and second anatomy engaging members to relieve undue pressure on the tissue. By way of further example, and where the surgical retractor is configured for change in separation between the first and second arms as described elsewhere herein, the clinician may operate the surgical retractor to reduce the extent of separation of the first and second anatomy engaging members to an extent sufficient to relieve undue pressure on the tissue while still maintaining sufficient extent of retraction.

The surgical retractor may be configured for change in separation between the first and second arms whereby separation between the first and second anatomy engaging members is changed.

In use, the separation between the first and second arms of the surgical retractor may be set to allow the first and anatomy engaging members to be received readily in an incision or wound. The clinician may then increase the separation between the first and second arms whereby the first anatomy engaging member bears against a first side of the incision or wound and the second anatomy engaging member bears against a second, opposite side of the incision or wound. The incision or wound may thus be retracted.

The material from which the anatomy engaging member is formed may be translucent.

As described above, the anatomy engaging member may comprise a main body, the main body formed from transparent material. The rest of the anatomy engaging member, such as a part attaching to the respective arm, may not be transparent.

More specifically, the anatomy engaging member may be formed substantially completely from transparent material. Substantially complete formation from transparent material may be appropriate where the anatomy engaging member is integrally formed.

The anatomy engaging member may be formed from a material selected from the group consisting of: polyester, and more specifically polycarbonate (PC) or polyethylene terephthalate (PET); acrylonitrile butadiene styrene (ABS); and poly methyl methacrylate (PMMA).

Further embodiments of the fifth aspect of the present invention may comprise one or more features of any previous aspect of the present invention.

According to a sixth aspect of the present invention there is provided a method of surgery on a human or animal subject involving use of a surgical retractor which comprises a support, first and second arms extending from a same side of the support and spaced apart from each other along the support, and first and second anatomy engaging members depending from the first and second arms respectively, the method of surgery comprising:

- disposing the surgical retractor relative to an incision or wound in the human or animal subject and such that the first and second anatomy engaging members are received in the incision or wound, wherein
- the first anatomy engaging member bears against first tissue at one side of the incision or wound and the second anatomy engaging member bears against second tissue at another side of the incision or wound,
- at least one of the first and second tissue is drawn back by said increase in separation, and
- at least one of the first and second anatomy engaging members is formed at least in part from a transparent material.

The method of surgery on the human or animal subject is practiced by a clinician. The clinician disposes the surgical retractor relative to an incision or wound in the human or animal subject and such that the first and second anatomy engaging members are received in the incision or wound. The first anatomy engaging member bears against first tissue at one side of the incision or wound and the second anatomy engaging member bears against second tissue at another side of the incision or wound. At least one of the first and second tissue is drawn back by said increase in separation. Formation of at least one of the first and second anatomy engaging members at least in part from a transparent material may confer the benefit described above, i.e. enable observation of tissue blanching underneath the anatomy engaging member, whereby the clinician may be able to determine if too much pressure is being applied to tissue during retraction and take appropriate action.

When the surgical retractor has been disposed appropriately relative to the incision or wound, the clinician may operate the surgical retractor to increase separation between the first and second arms where the surgical retractor is configured for change in separation between the first and second arms. Increase in separation between the first and second arms may cause increase in separation between the first and second anatomy engaging members comprised in the surgical retractor.

The clinician may operate the surgical retractor to increase separation between the first and second arms to an extent sufficient for the first anatomy engaging member to bear against first tissue at one side of the incision or wound and for the second anatomy engaging member to bear against second tissue at another side of the incision or wound. The step of operating the surgical retractor to increase separation between the first and second arms may further comprise at least one of the first and second tissue being drawn back, i.e. retracted, by the increase in separation.

Whether one, other or both of the first and second tissue is retracted may depend on the nature of the anatomy involved.

Further embodiments of the sixth aspect of the present invention may comprise one or more features of any previous aspect of the present invention.

BRIEF DESCRIPTION OF DRAWINGS

Further features and advantages of the present invention will become apparent from the following specific description, which is given by way of example only and with reference to the accompanying drawings, in which.

DESCRIPTION OF EMBODIMENTS

Figure 1:
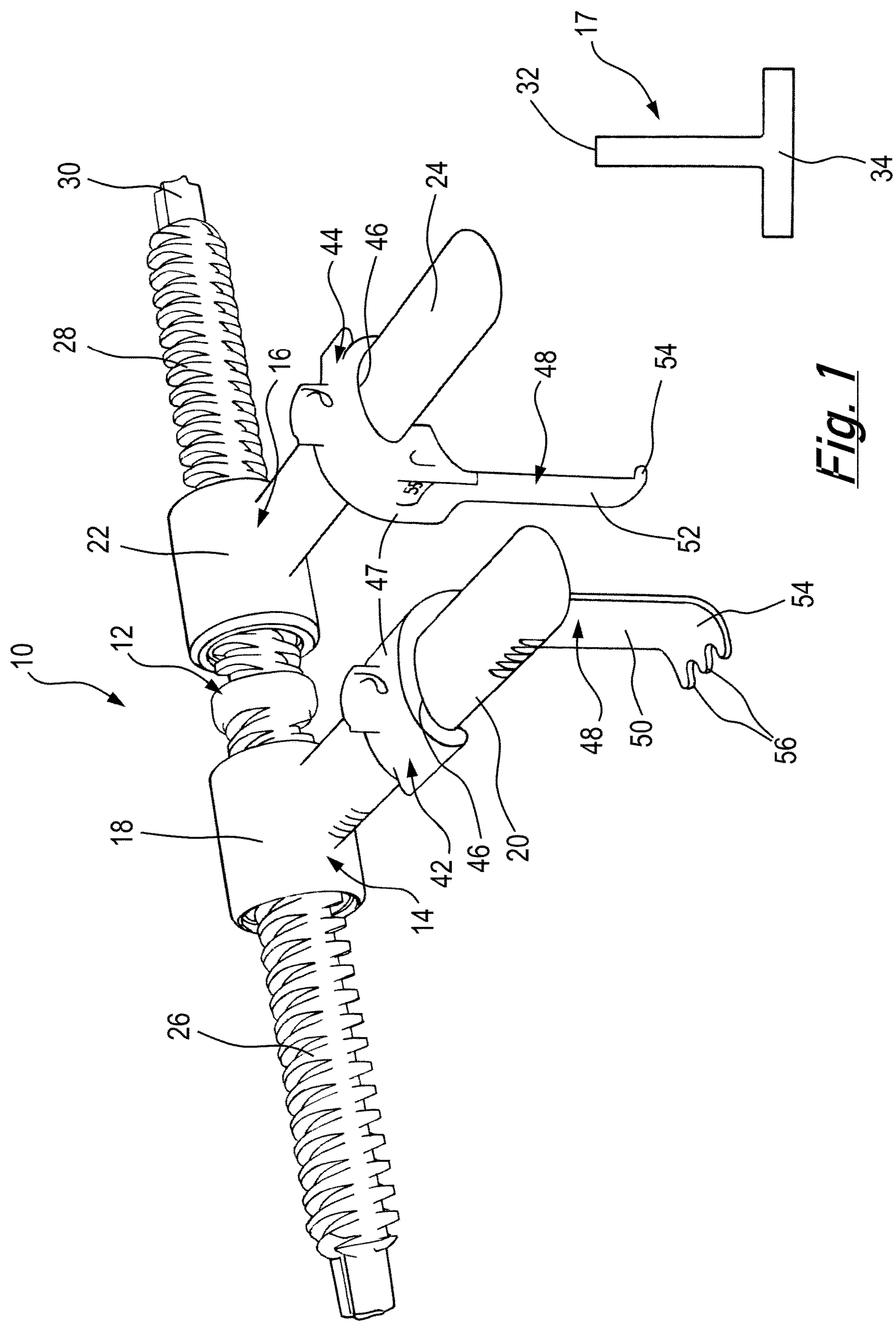
FIG. 1 is a perspective view of a surgical retractor according to an embodiment of the present invention.

A perspective view of a surgical retractor 10 according to an embodiment of the present invention is shown in FIG. 1. The surgical retractor 10 comprises an elongate support member 12, a first arm 14, and a second arm 16. Each of the first arm 14 and the second arm 16 is mounted for movement along the support member 12 as described further below. The surgical retractor 10 further comprises a tool 17 (in FIG. 1 the tool 17 is not to scale with the rest of the surgical retractor 10).

The first arm 14 comprises a proximal portion 18 which encircles the support member 12 and an elongate first arm member 20 which extends from the proximal portion 18. The first arm member 20 is integrally formed with the proximal portion 18. The second arm 16 comprises a proximal portion 22 which encircles the support member 12 and an elongate second arm member 24 which extends from the proximal portion 22. The second arm member 24 is integrally formed with the proximal portion 22. As can be seen from FIG. 1, the first and second arm members 20, 24 are aligned with each other. Each of the first and second arm members is substantially elliptical in cross-section. The width in cross section of each arm member is 15 mm and the height in cross section is 10 mm.

One half of the exterior of the support member 12 defines a first screw thread 26 and the other half of the exterior of the support member 12 defines a second screw thread 28. The first and second screw threads 26, 28 run in opposite directions to each other such that each runs towards its respective end of the support member 12. Each of the first and second screw threads 26, 28 has four starts. The interior of each of the two proximal portions 18, 22 defines a threaded profile which interengages with a respective one of the first and second screw threads 26, 28. Rotation of the support member 12 about its longitudinal axis moves each of the first and second arms 14, 16 in opposite directions along the support member 12 (i.e. together or apart depending on direction of rotation of the support member) by virtue of cooperation of the threaded profile on each proximal portion 18, 22 with a respective one of the first and second screw threads 26, 28.

As described above, the surgical retractor 10 further comprises a tool 17. An end of the support member 12 defines a plug 30 which extends in the longitudinal direction of the support member. The tool 17 is removably attached to the support member 12 by reception of the plug 30 of the support member in a socket 32 defined in a first end of the tool. The plug 30 and socket 32 are shaped to interlock with each other. The tool 17 comprises a hand grippable portion 34 at the second, opposite end thereof. When the plug 30 is received in the socket 32, the clinician rotates the tool 17 by way of the hand grippable portion 34. Rotation of the tool 17 is transmitted to the support member 12 by way of the interlocked plug 30 and socket 32. As described above, rotation of the support member 12 moves each of the first and second arms 14, 16 in opposite directions along the support member 12 whereby separation between the first and second arms changes.

The surgical retractor 10 further comprises first and second anatomy engaging members 42, 44. The first and second anatomy engaging members 42, 44 are of the same form and function. As can be seen from FIG. 1, the first anatomy engaging member 42 is attached to the first arm 18 and the second anatomy engaging member 44 is attached to the second arm 22 whereby each anatomy engaging member depends substantially orthogonally from its respective arm.

Each of the first and second anatomy engaging members 42, 44 defines an engaging member profile 46 at its proximal end whereby the anatomy engaging member is clipped to and thereby releasably engaged with an arm member 20, 24 while allowing for sliding movement of the anatomy engaging member along the arm member when so attached. The engaging member profile 46 is defined by an attachment portion 47 of the anatomy engaging member. The shape of the engaging member profile 46 corresponds to the profile of the arm member 20, 24 whereby the engaging member profile abuts against the arm member. The engaging member profile 46 has a main profile portion which extends across the upper surface of the arm member 20, 24. The engaging member profile 46 also has first and second lateral portions each at a respective end of the main profile portion. The first and second lateral portions are each shaped to extend over a side of the arm member 20, 24 and then a short distance across the lower surface of the arm member. The distal end of the first lateral portion therefore opposes the distal end of the second lateral portion with the distal ends of the first and second lateral portions spaced apart from each other across the lower surface of the arm member 20, 24.

The anatomy engaging member 42, 44 is attached to the arm member 20, 24 by sliding the engaging member profile 46 over the distal end of the arm member. Alternatively and in view of formation of the anatomy engaging member 42, 44 from a resilient material, the attachment portion 47 of the anatomy engaging member is pressed against the upper surface of the arm member whereby the distal ends of the first and second lateral portions are forced apart against the bias exerted by the resilient material to an extent sufficient to admit the arm member to the space defined by the engaging member profile 46. When the arm member is admitted properly in the space defined by the engaging member profile 46, the distal ends of the first and second lateral portions move together again under bias exerted by the resilient material whereby the anatomy engaging member 42, 44 is attached securely to the arm member 20, 24 whilst allowing for movement of the anatomy engaging member along the arm member.

Each of the first and second anatomy engaging members 42, 44 has a main body 48 which is attached at its proximal end to the attachment portion 47. The main body 48 has the form of a substantially rectangular plate which defines a curve across its width. As may be seen from FIGS. 2A and 2B, an exterior face 50 of the main body 48 is convex and an interior face 52 of the main body is concave. Each of the first and second anatomy engaging members 42, 44 defines a foot portion 54 at a distal end thereof. The foot portion 54 extends generally orthogonally to the distal end of the main body 48. Each foot portion 48 defines two recesses 56 at a distal end thereof with the two recesses spaced apart in the transverse direction, i.e. across the width of the anatomy engaging member.

Figure 2A:
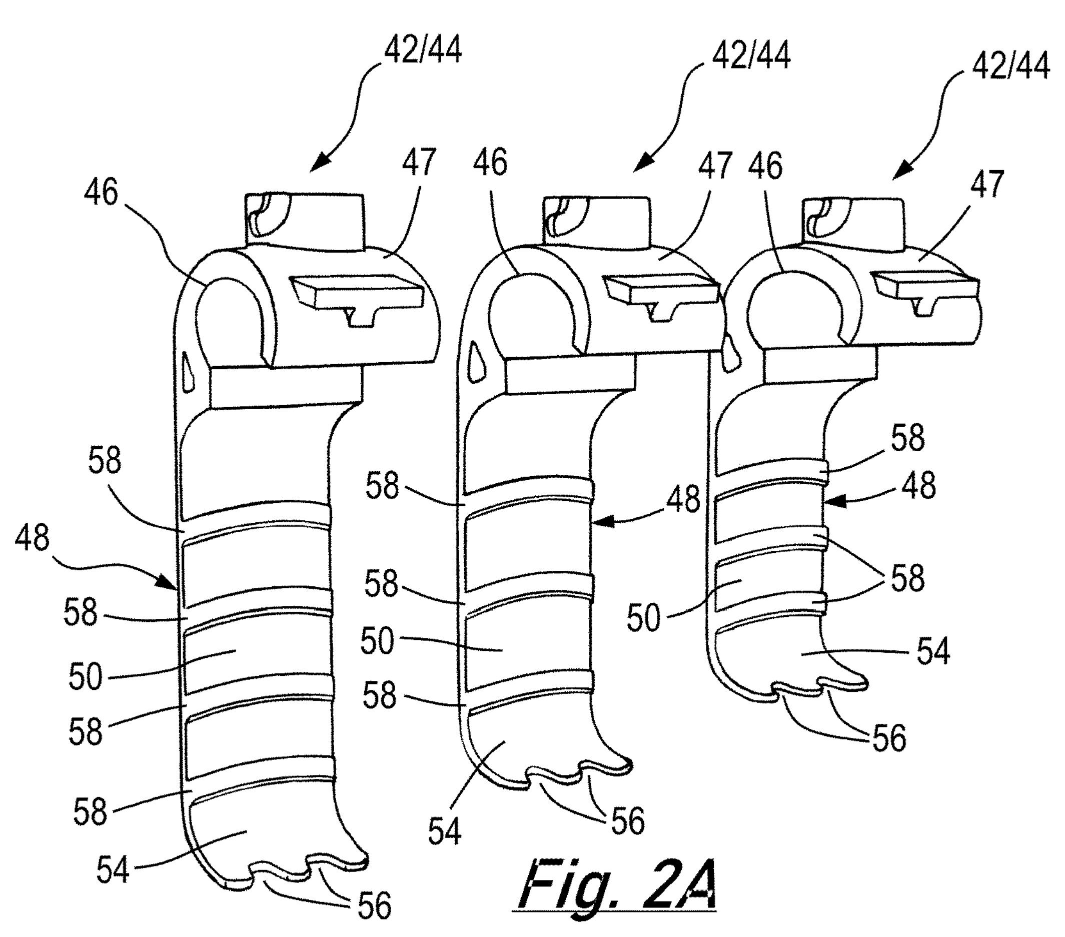
FIG. 2A is a perspective view from one side of three anatomy engaging members selectively comprised in the surgical retractor of FIG. 1.
Figure 2B:
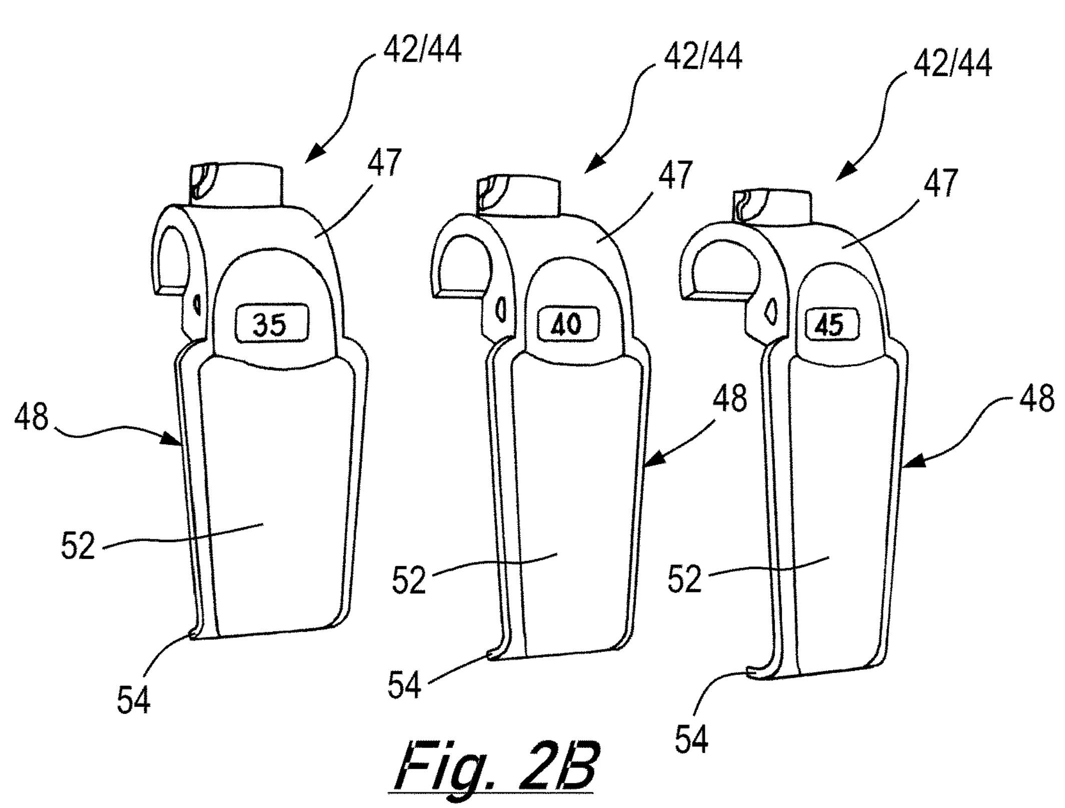
FIG. 2B is a perspective view from another side of the three anatomy engaging members of FIG. 2A.

FIGS. 2A and 2B provide detailed views of the first and second anatomy engaging members 42, 44. FIG. 2A is a view of the exterior face 50 of three anatomy engaging members 42, 44 which are selectively attached to arms 14, 16 of the surgical retractor 10 of FIG. 1. FIG. 2B is a view of the interior face 52 of the three anatomy engaging members 42, 44 of FIG. 2A. The three anatomy engaging members 42, 44 of FIGS. 2A and 2B differ from one another in respect of their length. One of the three anatomy engaging members 42, 44 of FIGS. 2A and 2B is selected for each of the first and second arms 14, 16 of the surgical retractor 10 depending on the depth of the incision or wound to be retracted.

Each of the three anatomy engaging members 42, 44 shown in FIGS. 2A and 2B is as described above with reference to FIG. 1. Further to this, plural elongate protrusions 58 are defined on the exterior face 50 and on the same side of the main body 48 from which the foot portion 54 extends. Each elongate protrusion 58 extends transversely on the anatomy engaging member 42, 44. Each elongate protrusion 58 is defined by first and second protrusion sides and a protrusion land.

The first and second protrusion sides extend up from the exterior face, and the protrusion land extends between the distal end of the first protrusion side and the distal end of the second protrusion side. The first and second protrusion sides are substantially parallel with each other. The protrusion land is substantially linear in the longitudinal direction of the anatomy engaging member 42, 44. Further to this, the protrusion land is arcuate in the transverse direction. The protrusion land is convex with curvature of the protrusion land greatest towards each end of the protrusion land. The height of the first and second protrusion sides thus decreases as one moves towards the ends of the protrusion 58. The height of the first and second protrusion sides decreases to substantially zero at each end of the protrusion land.

Each protrusion 58 defines an acute angle of 30 degrees between a part of the exterior face 50 on the side of the protrusion nearer to the attachment portion 47 than a part of the exterior face on the other side of the protrusion. The protrusion therefore protrudes away from the exterior face 50 and in an oblique direction away from a distal end of the anatomy engaging member 42, 44. Each protrusion 58 defines an obtuse angle of 150 degrees between a part of the exterior face 50 on the side of the protrusion nearer to a distal end of the anatomy engaging member 42, 44 than a part of the exterior face on the other side of the protrusion. As can be seen from FIG. 2A, the plural protrusions 58 are spaced apart evenly in the longitudinal direction along the main body 48 of the anatomy engaging member 42, 44.

The retractor 10 is formed substantially completely of a plastics material. Most of the retractor 10 with the exception of the first and second anatomy engaging members 42, 44 and the tool 17 is formed from GS Ixef® 1022 from Solvay S. A. By way of further exception, the threaded profile of each proximal portion 18, 22 is formed from polyoxymethylene (POM). More specifically a collar formed of POM which defines the threaded profile on its interior surface is received in and clipped into place within a bore defined by the proximal portion 18, 22. In another form, the threaded profile of each proximal portion 18, 22 is formed from GS Ixef® 1022 whereby there is no need for the collar. Parts of the retractor are integrally formed by injection moulding. For example, the first and second arms 14, 16 are each integrally formed. By way of another example, the support member 12 is integrally formed. By way of further example, the tool 17 is integrally formed. The tool 17 and the first and second anatomy engaging members 42, 44 are formed from polycarbonate (PC). More specifically, the tool 17 and the first and second anatomy engaging members 42, 44 are formed from Makrolon® 2458 from Bayer MaterialScience AG, 51368 Leverkusen, Germany. In a first embodiment, the first and second anatomy engaging members 42, 44 are formed from opaque polycarbonate (PC). In a second embodiment, the first and second anatomy engaging members 42, 44 are formed from transparent polycarbonate (PC). In further embodiments, the first and second anatomy engaging members 42, 44 are formed from a plastics material other than polycarbonate (PC). More specifically, the first and second anatomy engaging members 42, 44 are formed from transparent polyethylene terephthalate (PET), transparent acrylonitrile butadiene styrene (ABS) or transparent poly methyl methacrylate (PMMA).

Figure 3:
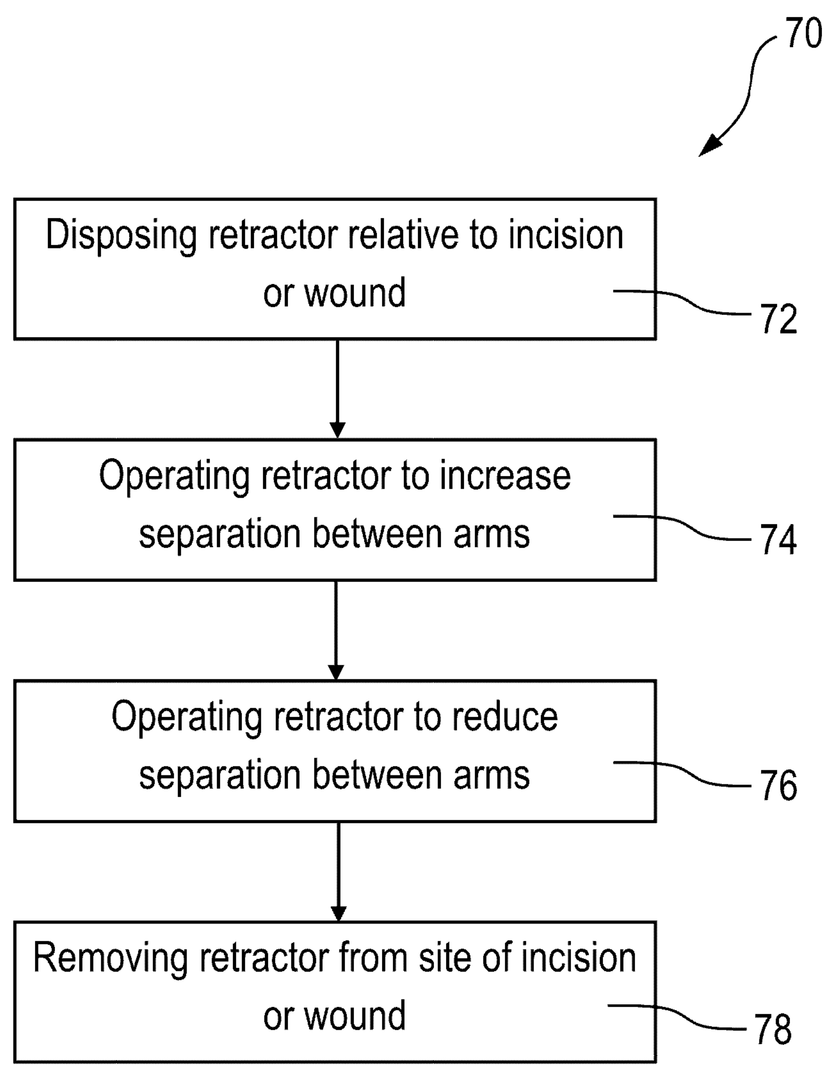
FIG. 3 is a flow chart representation of a method of surgery involving use of the surgical retractor of FIG. 1.

A flow chart representation of a method of surgery 70 involving use of the surgical retractor 10 of FIG. 1 is shown in FIG. 3. The method of surgery 70 comprises disposing the surgical retractor 10 relative to an incision or wound in a human or animal subject and such that the first and second anatomy engaging members 42, 44 are received in the incision or wound 72. The surgical retractor 10 is operated by rotation of the support member 12 such that the first and second anatomy engaging members 42, 44 are sufficiently close to each other that the first and second anatomy engaging members can be received readily in the incision or wound. Insertion of the first and second anatomy engaging members 42, 44 into the incision or wound is eased by the upward angulation of the plural protrusions 58 described above. Furthermore, the coefficient of friction of the material of the first and second anatomy engaging members 42, 44 provides for ease of movement of tissue over the first and second anatomy engaging members in the longitudinal direction of the first and second anatomy engaging members. When the first and second anatomy engaging members 42, 44 are received in the incision or wound, the surgical retractor 10 is moved in the plane of the incision or wound if need be and until the first and second anatomy engaging members are positioned appropriately. During such adjustment of position, the coefficient of friction of the material of the first and second anatomy engaging members 42, 44 provides for ease of movement of tissue over the first and second anatomy engaging members in the transverse direction of the first and second anatomy engaging members.

The clinician then operates the surgical retractor 10 by means of the tool 17 to rotate the support member 12 to thereby increase separation between the first and second arms 14, 16, 74. This increases separation between the first and second exterior faces 50 to an extent sufficient for the first exterior face to bear against and retract first tissue at one side of the incision or wound and for the second exterior face to bear against and retract second tissue at another side of the incision or wound. This step may result in movement in the transverse direction of tissue over the first and second anatomy engaging members 42, 44 with such transverse movement being eased by the coefficient of friction of the material of the first and second anatomy engaging members. Meanwhile, the protrusions 58 press into or are received under and thereby interengage with tissue to thereby present resistance to the first and second anatomy engaging members 42, 44 being pushed out of the incision or wound by reactive pressure from the tissue being retracted.

Depending on the application, the foot portions 54 fit underneath anatomy whereby the anatomy is gathered up and held by the foot portion. The foot portion 54 is useful for engaging with a substantial mass of anatomy, such as muscle tissue, or perhaps even for fitting underneath or resting upon bone. In the embodiments in which the first and second anatomy engaging members 42, 44 are formed from transparent plastics material, the clinician can observe the tissue underneath the first and second anatomy engaging members. If the tissue underneath the first and second anatomy engaging members 42, 44 blanches, which is an indication of distress being caused to the tissue, the clinician operates the surgical retractor 10 to reduce the separation between the arms 14, 16 to small extent yet sufficient extent to relieve pressure on the distressed tissue.

When need for the surgical retractor 10 has passed, the clinician operates the surgical retractor 10 to reduce separation between the arms 14, 16 to sufficient extent to allow for ease of removal of the first and second anatomy engaging members 42, 44 from the incision or wound 76. The surgical retractor 10 is then removed by the clinician from the site of the incision or wound 78.

A perspective view of a cervical retractor 110 according to a further embodiment of the present invention is shown in FIG. 2. The cervical retractor 110 comprises an elongate support member 112, a first arm 114, and a second arm 116. Each of the first and second arms 114, 116 is mounted for movement along the support member 112 in the same fashion as described above with reference to the embodiment of FIG. 1. The elongate support member 112, and the first and second arms 114, 116 are formed from acetal. The elongate support member 112 is 110 mm long. The cervical retractor 110 further comprises a tool 117, which is formed from polycarbonate and more specifically Makrolon® 2458 from Bayer MaterialScience AG, 51368 Leverkusen, Germany.

The first arm 114 comprises a proximal portion 118 which encircles the support member 112 and an elongate first arm member 120 which extends from the proximal portion 118. The first arm member 120 is integrally formed with the proximal portion 118. The second arm 116 comprises a proximal portion 122 which encircles the support member 112 and an elongate second arm member 124 which extends from the proximal portion 122. The second arm member 124 is integrally formed with the proximal portion 122. Each of the first and second arm members 120, 124 is 96 mm long. As can be seen from FIG. 4, the first and second arm members 120, 124 are aligned with each other. Each of the first and second arm members is substantially elliptical in cross-section. The width in cross section of each arm member 120, 124 is 14 mm and the height in cross section is 8 mm.

One half of the exterior of the support member 112 defines a first screw thread 126 and the other half of the exterior of the support member 112 defines a second screw thread 128. The first and second screw threads 126, 128 run in opposite directions to each other such that each runs towards its respective end of the support member 112. Each of the first and second screw threads 126, 128 has four starts. The interior of each of the two proximal portions 118, 122 defines a threaded profile which interengages with a respective one of the first and second screw threads 126, 128. The threaded profile portion each of the two proximal portions 118, 122 is integrally formed with the respective proximal portion. There is therefore no need for a collar to define the threaded profile.

As per the embodiment of FIG. 1, rotation of the support member 112 about its longitudinal axis moves each of the first and second arms 114, 116 in opposite directions along the support member 112 (i.e. together or apart depending on direction of rotation of the support member) by virtue of cooperation of the threaded portion on each proximal portion 118, 122 with a respective one of the first and second screw threads 126, 128.

The cervical retractor 110 further comprises a hand grippable rotation device 217, which is formed from polycarbonate and more specifically Makrolon® 2458 from Bayer MaterialScience AG, 51368 Leverkusen, Germany. An end of the support member 112 defines a plug 130 which extends in the longitudinal direction of the support member. The rotation device 217 is removably attached to the support member 112 by reception of the plug 130 of the support member in a correspondingly shaped socket 132 defined in the rotation device. The plug 130 and socket 132 are shaped to interlock with each other. The rotation device 217 defines a hand grippable portion 134. When the plug 130 is received in the socket 132, the clinician rotates the rotation device 217 by way of the hand grippable portion 134. Rotation of the rotation device 217 is transmitted to the support member 112 by way of the interlocked plug 130 and socket 132. Rotation of the support member 112 moves each of the first and second arms 114, 116 in opposite directions along the support member 112 whereby separation between the first and second arms changes.

The cervical retractor 110 further comprises first and second anatomy engaging members 142, 144. The first and second anatomy engaging members 142, 144 are of the same form and function. As can be seen from FIG. 4, the first anatomy engaging member 142 is attached to the first arm 118 and the second anatomy engaging member 144 is attached to the second arm 122 whereby each anatomy engaging member depends substantially orthogonally from its respective arm member. The form and function of each of the first and second anatomy engaging members 142, 144 is as described above for the first and second anatomy engaging members 42, 44 of the embodiment of FIG. 1.

The cervical retractor 110 yet further comprises a first bridging part 220 and a second bridging part 222. The first and second bridging parts 220, 222 are formed from acetal. Each of the first and second bridging parts 220, 222 is releasably attached to the first and second arms 116, 118 at locations spaced apart along the first and second arms. Furthermore, the first and second bridging parts 220, 222 are movable along the first and second arms 116, 118. Each of the first and second bridging parts 220, 222 comprises first and second bridging part components. A proximal end of the first bridging part component defines a bore which is shaped to receive a proximal end of the second bridging part component to thereby provide for change in length of the bridging part 220, 222 by telescopic adjustment. As the separation of the first and second arms 116, 118 is increased by rotation of the support member 114, the proximal end of the second bridging part component is withdrawn from the bore defined in the end of the first bridging part component. As the separation of the first and second arms 116, 118 is decreased by rotation of the support member 114 in the opposite direction, the proximal end of the second bridging part component is received further in the bore defined in the end of the first bridging part component.

Each bridging part 220, 222 is configured to releasably attach at each of its first and second ends to a respective arm 116, 118. Each of the first and second ends of the bridging part 220, 222 is shaped to cooperate with the profile of the respective arm member to resist separation of the bridging part from the arm member. Each bridging part 220, 222 is attached to an arm 116, 118 by sliding the respective one of the first and second ends over the distal end of the arm member. Teeth 178 extend along the arm members of the first and second arms 116, 118, and each of the first and second ends of each bridging part 220, 222 define a movable finger 182. The finger 182 constitutes a pawl which engages with the teeth 178 on the arm member whereby finger and teeth form a ratchet mechanism which regulates movement of the bridging part 220, 222 along the arm member. The finger 182 engages with the teeth by being urged against the teeth by inherent spring bias. The finger 182 is moved by the clinician to disengage from the teeth to thereby allow free movement of the bridging parts 220, 222 along the arm member. Furthermore, the teeth 178 are shaped to allow the finger 182 when not disengaged by the clinician to ride over the teeth when separation between the two bridging parts 220, 222 is increased and to present resistance to movement of the finger over the teeth in the opposite direction, i.e. the direction resulting in reduction in separation between the two bridging parts.

The cervical retractor 110 also comprises a third anatomy engaging member 224 and a fourth anatomy engaging member 226. Each of the third and fourth anatomy engaging members 224, 226 is of the same form as the first and second anatomy engaging members 142, 144 described above. Each of the third and fourth anatomy engaging members 224, 226 is releasably attached to a respective one of the first and second bridging parts 220, 222. The first to fourth anatomy engaging members 142, 144, 220, 222 are formed from transparent polycarbonate and more specifically Makrolon® 2458 from Bayer MaterialScience AG, 51368 Leverkusen, Germany. A main body of each of the first to fourth anatomy engaging members 142, 144, 220, 222 is 35 to 55 mm long. The first to fourth anatomy engaging members 142, 144, 220, 222 provide for retraction in a first direction parallel to the longitudinal axis of the support member 114 by rotation of the support member and in a second direction substantially orthogonal to the first direction by way of movement apart of the first and second bridging parts 220, 222.

Figure 4:
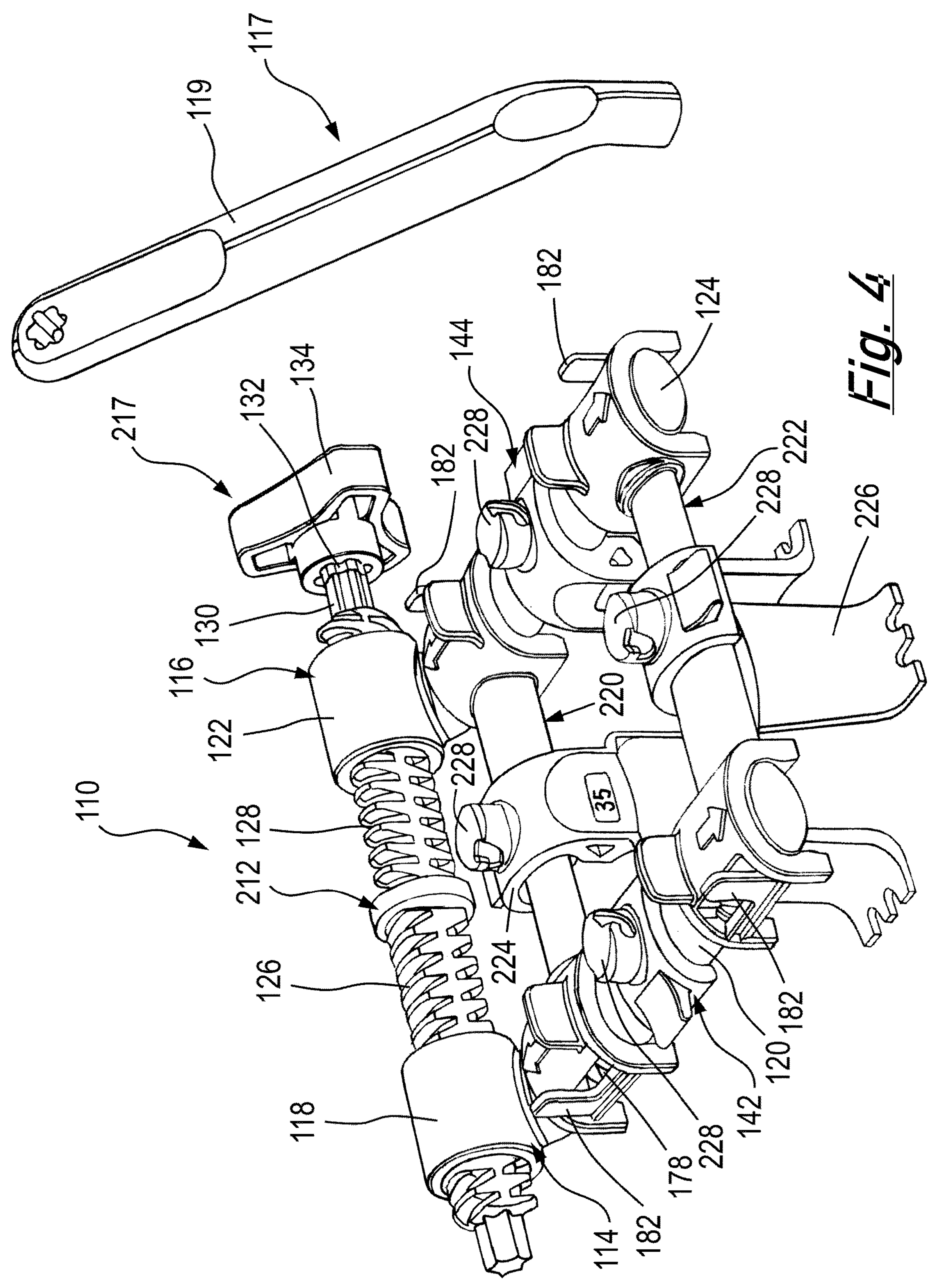
FIG. 4 is a perspective view of a cervical retractor according to a further embodiment of the present invention.

As can be seen from FIG. 4, the proximal end of each of the first to fourth anatomy engaging members 142, 144, 220, 222 defines a protrusion 228 which is shaped to be received in and to interlock with a socket defined in an end of the tool 117. Connection of the tool 117 with the protrusion 228 of an anatomy engaging member in this fashion enables the clinician to apply leverage to the anatomy engaging member by way of a handle 119 of the tool to thereby release the anatomy engaging member from an arm member 120, 124 or bridging part 220, 222.

The cervical retractor 110 is used in the same fashion as the surgical retractor of FIG. 1, as described above with reference to FIG. 3, and where the cervical retractor 110 is used for soft tissue retraction in the like of anterior cervical discectomy or fusion procedures.

The invention claimed is:

1. A surgical retractor, comprising:

a support;

first and second arms extending from a same side of the support and spaced apart from each other along the support;

a first anatomy engaging member having a first interior face and a first exterior face; and a second anatomy engaging member having a second interior face and a second exterior face, wherein:

the first anatomy engaging member depends along its length from the first arm whereby the first exterior face faces away from the second anatomy engaging member;

the second anatomy engaging member depends along its length from the second arm whereby the second exterior face faces away from the first anatomy engaging member;

each of the first and second exterior faces integrally defines on their surfaces at least one elongate protrusion across the surface of the respective exterior faces, the elongate protrusion having an elongate axis extending transversely on the surface of the respective exterior face of the respective anatomy engaging member whereby the elongate protrusion is integral to the exterior face of the respective anatomy engaging member;

each elongate protrusion has first and second protrusion sides extending up from and transversely across the surface of the respective exterior face, the first protrusion side closer than the second protrusion side to a proximal end of the respective anatomy engaging member;

each elongate protrusion defines an acute angle with the respective exterior face, the acute angle defined between the first protrusion side and a first part of the exterior face on a first side of the elongate protrusion, the first part of the exterior face nearer to the proximal end of the respective anatomy engaging member than a second part of the exterior face on a second side of the elongate protrusion; and the first and second protrusion sides are substantially parallel with each other.

2. The surgical retractor according to claim 1, in which each of the first and second arms extends from a respective location, the two locations spaced apart from each other along the support.

3. The surgical retractor according to claim 1, in which the surgical retractor is configured for change in separation between the first and second arms along the support, whereby separation between the first and second exterior faces is changed.

4. The surgical retractor according to claim 3, in which change in separation between the first and second arms is by movement of at least one of the first and second arms along the support.

5. The surgical retractor according to claim 1, in which the elongate protrusion is defined by the first and second protrusion sides and a protrusion land, the protrusion land extending between the distal ends of the first and second protrusion sides.

6. The surgical retractor according to claim 5, in which the protrusion land is convex in the transverse direction whereby the height of the first and second protrusion sides above the respective exterior face decreases towards the ends of the elongate protrusion.

7. The surgical retractor according to claim 6, in which the height of the first and second protrusion sides above the respective exterior face decreases to substantially zero at each end of the protrusion land.

8. The surgical retractor according to claim 5, in which the protrusion land is substantially linear in a longitudinal direction of the respective anatomy engaging member.

9. The surgical retractor according to claim 1, in which each elongate protrusion defines an obtuse angle with the respective exterior face, the obtuse angle defined between the second protrusion side and the second part of the exterior face.

10. The surgical retractor according to claim 9, in which the obtuse angle is between 145 degrees and 155 degrees.

11. The surgical retractor according to claim 10, in which the obtuse angle is 150 degrees.

12. The surgical retractor according to claim 1, in which at least one of the first and second exterior faces defines plural elongate protrusions spaced apart in a longitudinal direction of the respective anatomy engaging member.

13. The surgical retractor according to claim 12, in which the plural elongate protrusions are not contiguously adjacent each other.

14. The surgical retractor according to claim 13, in which a spacing between adjacent protrusions is wider than a width in a longitudinal direction of any of the plural elongate protrusions.

15. The surgical retractor according to claim 1, in which the anatomy engaging member comprises a main body which defines the respective exterior and interior faces, the main body having the form of an elongate plate.

16. The surgical retractor according to claim 15, in which the main body is arcuate in the transverse direction whereby the exterior face is convex and the interior face is concave.

17. The surgical retractor according to claim 1, in which each of the first and second anatomy engaging members is attached to the respective arm for sliding movement of the anatomy engaging member along the arm.

18. The surgical retractor according to claim 1, in which the support is elongate, the first and second arms are attached at first and second locations respectively on the elongate support, the first and second locations are spaced apart from each other, and at least one of the first and second arms is attached to the elongate support for movement along the elongate support, and in which the elongate support and the arm define cooperating surface profiles which move the arm along the elongate support.

19. The surgical retractor according to claim 1, in which the first and second protrusion sides are both at an acute angle to the first part of the exterior face.

20. The surgical retractor according to claim 1, in which each elongate protrusion is immovable relative to the respective anatomy engaging member.

21. A surgical retractor, comprising:

a support;

first and second arms extending from a same side of the support and spaced apart from each other along the support;

a first anatomy engaging member having a first interior face and a first exterior face; and a second anatomy engaging member having a second interior face and a second exterior face, wherein:

the first anatomy engaging member depends along its length from the first arm whereby the first exterior face faces away from the second anatomy engaging member;

the second anatomy engaging member depends along its length from the second arm whereby the second exterior face faces away from the first anatomy engaging member;

each of the first and second exterior faces integrally defines on their surfaces at least one elongate protrusion across the surface of the respective exterior faces, the elongate protrusion having an elongate axis extending transversely on the surface of the respective exterior face of the respective anatomy engaging member whereby the elongate protrusion is integral to the exterior face of the respective anatomy engaging member;

each elongate protrusion has first and second protrusion sides extending up from and transversely across the surface of the respective exterior face, the first protrusion side closer than the second protrusion side to a proximal end of the respective anatomy engaging member;

each elongate protrusion defines an acute angle with the respective exterior face, the acute angle defined between the first protrusion side and a first part of the exterior face on a first side of the elongate protrusion, the first part of the exterior face nearer to the proximal end of the respective anatomy engaging member than a second part of the exterior face on a second side of the elongate protrusion; and the acute angle is between 25 degrees and 35 degrees.

22. The surgical retractor according to claim 21, in which the acute angle is 30 degrees.

* * * * *